(12) United States Patent
Pozzo

(10) Patent No.: US 6,481,639 B1
(45) Date of Patent: Nov. 19, 2002

(54) VOLATILE SUBSTANCE DIFFUSER WITHOUT PERSISTENCE

(75) Inventor: Michel Pozzo, Neuilly-sur-Seine (FR)

(73) Assignee: Ateliers de Conceptions et d'Innovations Industrielles, Courbevoie (FR)

( * ) Notice: Subject to any disclaimer, the term of this patent is extended or adjusted under 35 U.S.C. 154(b) by 0 days.

(21) Appl. No.: 09/600,869

(22) PCT Filed: Jan. 22, 1999

(86) PCT No.: PCT/FR99/00135
§ 371 (c)(1),
(2), (4) Date: Aug. 9, 2000

(87) PCT Pub. No.: WO99/40950
PCT Pub. Date: Aug. 19, 1999

(30) Foreign Application Priority Data

Feb. 10, 1998 (FR) .............................. 98 01526

(51) Int. Cl.[7] .................................................. A24F 25/00
(52) U.S. Cl. ......................... 239/47; 239/49; 239/51.5; 239/53; 239/55; 239/57; 239/58
(58) Field of Search .............................. 239/34, 41, 42, 239/43, 47, 49, 51.5, 53, 55, 57, 58, 59

(56) References Cited

U.S. PATENT DOCUMENTS

| | | | | |
|---|---|---|---|---|
| 2,025,657 A | * | 12/1935 | Ganz | ........................... 239/55 |
| 2,086,631 A | * | 7/1937 | Munro | ........................ 222/463 |
| 2,215,988 A | * | 9/1940 | Vivadou et al. | ............... 239/59 |
| 3,924,807 A | * | 12/1975 | Morgan | ........................ 239/55 |
| 4,146,566 A | | 3/1979 | Gaiser | |
| 4,149,675 A | * | 4/1979 | Van Breen et al. | ........... 239/57 |
| 4,247,042 A | * | 1/1981 | Schimanski et al. | .......... 239/47 |
| 4,695,434 A | | 9/1987 | Spector | |
| 4,944,455 A | * | 7/1990 | Haust et al. | .................. 239/59 |
| 5,014,913 A | | 5/1991 | Hoyt et al. | |
| 5,417,929 A | * | 5/1995 | Kita | ........................... 422/123 |
| 6,029,900 A | * | 2/2000 | Quinones | ..................... 239/47 |

FOREIGN PATENT DOCUMENTS

| | | |
|---|---|---|
| DE | 295 10 619 | 11/1996 |
| FR | 1 500 142 | 1/1968 |
| GB | 2254557 | * 10/1992 |

* cited by examiner

Primary Examiner—Lesley D. Morris
Assistant Examiner—Dinh Q. Nguyen
(74) Attorney, Agent, or Firm—Jacobson Holman PLLC

(57) ABSTRACT

The invention concerns a volatile substance diffuser (102) comprising a body (104) with an aperture (111), and a reservoir (120) of product, comprising a volatile substance, the reservoir (102) being mounted mobile in the body (104) between a diffusing position enabling a gas to circulate through the product, then through the aperture (111) and a closed position wherein the product is isolated from the aperture (111), the reservoir and the body having respective surfaces (122,116) extending opposite each other. One of the surfaces (122) is spherical.

18 Claims, 8 Drawing Sheets

FIG_4

FIG_5

FIG_6

FIG_7

FIG_8

FIG_9

FIG_10  FIG_11

FIG_12  FIG_13

FIG_15

FIG_14  FIG_16

FIG_21

FIG_22

FIG_23

FIG_24

FIG_25

FIG_26

VOLATILE SUBSTANCE DIFFUSER WITHOUT PERSISTENCE

BACKGROUND OF THE INVENTION

1. Field of the Invention

The invention relates to volatile-substance diffusers.

2. Prior Art

Patent EP-0 104 758 discloses a volatile-substance diffuser comprising a body and a cartridge of a product saturated with a volatile substance. The body can accept the cartridge removably. A radiator allows the air under the cartridge to be heated to force it to pass through the cartridge and escape through an upper opening in the body in order to diffuse the substance. To stop diffusion, the cartridge has to be removed from the body, then the cartridge has to be hermetically sealed by a protective member. These operations are relatively lengthy to perform. What is more, the substance continues to diffuse when the cartridge is removed from the body as long as it is not covered with the protective member. Diffusion therefore stops very gradually over a fairly long period of time and, in particular, after the user wishes it to stop. A persistent smell thus remains, and it is preferable to wait until this has completely disappeared before diffusing another substance.

Another source, document FR-1 500 142, discloses a smell diffuser comprising two concentric cylindrical tubes with lateral openings and able to rotate so as to deliberately make their openings coincide so that the smell of a substance housed in the inner tube can be diffused. Using this device, eliminating the effect of a persistent smell entails having an airtight seal between the two tubes. Now, this seal is of a form that is relatively complicated to produce.

One object of the invention is to provide a diffuser which allows diffusion to be stopped abruptly and which is easy to manufacture.

With a view to achieving this object, the invention envisages a diffuser of a volatile substance comprising a body which has at least one opening and a reservoir for a product containing a volatile substance, the reservoir being mounted so that it can move in the body between a diffusing position which allows a gas to flow through the product, then into the opening, and a closed position in which the product is isolated from the opening, the reservoir and the body having respective faces extending facing each other, in which one of the faces is spherical.

Thus, having a spherical face, the seal may have a form that is simple to produce, for example a circular form. As the seal is a total seal, smell is not diffused at all in the closed position. Placing the reservoir in the closed position allows diffusion of the volatile substance to be stopped abruptly, with no persistence effect. It is thus possible to swiftly alternate the diffusion of different substances. What is more, diffusion can be stopped simply and quickly.

Advantageously, the spherical face is that of the reservoir.

Advantageously, the reservoir can move in terms of rotation with respect to the body.

Advantageously, the reservoir can move so that it turns on itself so that the reservoir occupies the same place in the body in its diffusing position and in its closed position.

Thus, the change in position is compatible with a small space requirement inside the body.

Advantageously, the reservoir can move about an axis of rotation perpendicular to a direction in which the gas flows through the product.

Advantageously, the faces each have symmetry of revolution about the axis of rotation.

Advantageously, the faces are spherical.

Advantageously, the reservoir has a spherical interior face.

Advantageously, with the opening being a first opening, the body has a second opening designed so that, in the diffusing position, the gas flows into the second opening, then through the product, then into the first opening.

Advantageously, the diffuser comprises at least one element which makes a seal between the body and the reservoir in the closed position.

Advantageously, the reservoir comprises a removable cartridge containing the product.

Advantageously, the product comprises granules containing the volatile substance in the adsorbed state.

The granules can adsorb a large amount of volatile substance. The spaces between the granules make it possible to offer a broad area for exchange between the circulating gas and the granules for diffusing the substance.

Advantageously, the reservoir has a wall exhibiting orifices, each having a contour shaped such that it forms a passage for gas when a spherical granule is resting against the orifice.

Thus, the wall holds the granules back whatever the position of the wall, for example if it is vertical, and the orifices are not closed off by the granules.

Advantageously, the orifices have a skewed circular contour.

Advantageously, the wall is undulating.

Thus, the orifices are given a skewed shape in a particularly simple way.

The invention also envisages a device for diffusing a volatile substance comprising at least one diffuser according to the invention, and a support designed to accept the diffuser or diffusers simultaneously.

Advantageously, the support is designed to hold the or each diffuser by clipping-together.

Advantageously, the support comprises means for controlling the position of the reservoir of the or each diffuser.

Advantageously, the support comprises means for circulating a gas through the or each diffuser in the diffusing position.

This may be a blower, which avoids heating up the products and degrading the substances that are to be diffused, or better still a turbine which has the additional advantage of being quieter.

Advantageously, the support is, for example, an organ pipe and comprises at least two diffusers, the gas-circulating means being common to the diffusers.

Advantageously, the diffusion device comprises polarizing means for accepting the diffuser in the support in at least one predetermined position.

Advantageously, the diffusion device comprises polarizing means for accepting the diffuser in the support in at least one predetermined diffuser in the support.

These together with other objects and advantages which will become subsequently apparent reside in the details of construction and operation as more fully hereinafter described and claimed, reference being had to the accompanying drawings forming a part hereof, wherein like numerals refer to like parts throughout.

Other features and advantages of the invention will become more apparent from the description which will follow of two preferred embodiments given by way of nonlimiting examples. In the appended drawings.

DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figures 1, 2, 3:
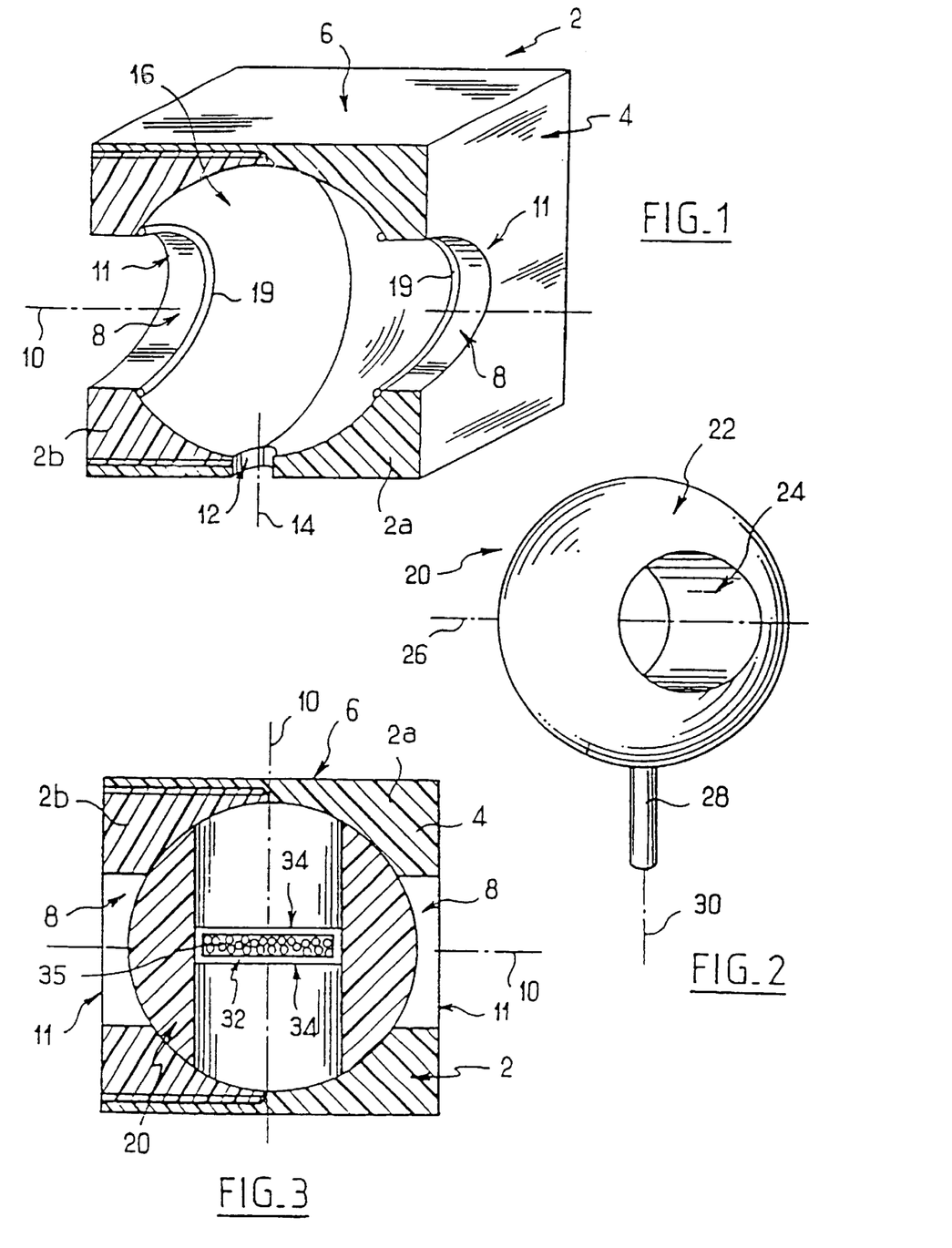
FIG. 1 is a view in axial section and in perspective of a diffuser body according to a first embodiment of the invention.
FIG. 2 is a perspective view of a spool of the diffuser of FIG. 1.
FIG. 3 is a view in axial section showing the body and the spool of FIGS. 1 and 2 assembled in the closed position.

With reference to FIGS. 1 and 3, a diffuser 2 according to the first embodiment of the invention comprises a body 4 with an exterior face 6 of any shape, for example cubic. The body 4 has a cylindrical duct 8 of axis 10, opening to two opposed front and rear faces of the body, defining two, front and rear, openings 11 and passing through the center of the body. The body 4 also has a cylindrical duct 12 of axis 14 perpendicular to the axis 10 and intersecting the latter geometrically at the center of the body. The duct 12 opens onto an exterior lower face of the body.

The body 4 has an interior face 16 with symmetry of revolution about the axis 14. In this particular instance, this face 16 is spherical and has its center at the center of the body. It geometrically intersects the ducts 8 and 12. The body 4 has two seals in the form of circular strips 19 of elastomer arranged on the spherical face 16 and contiguous with the two parts of the duct 8 which are separated from one another by the spherical face 16.

With reference to FIGS. 2 and 3, the diffuser 2 also comprises a spool 20 which has a spherical exterior face 22 of roughly the same radius as the spherical interior face 16 of the body 4, so that the spool 20 can be placed in the body 4, the two spherical faces 16, 22 facing one another. The spool 20 has a cylindrical duct 24 of axis 26 passing diametrically right through the sphere. The spool 20 has a shaft 28 of axis 30 oriented radially with respect to the center of the sphere and at right angles to the axis 26. The shaft 28 projects from the spherical exterior face 22.

Figure 4:
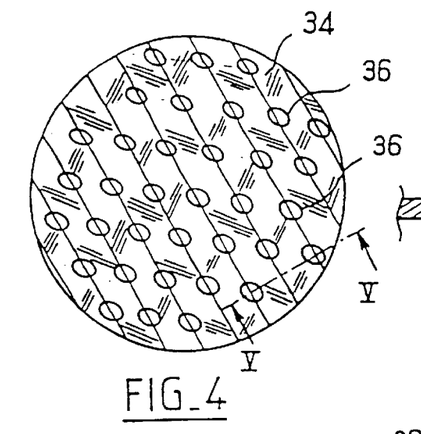
FIG. 4 is a plan view of the wall of the cartridge of FIG. 3.
Figure 5:
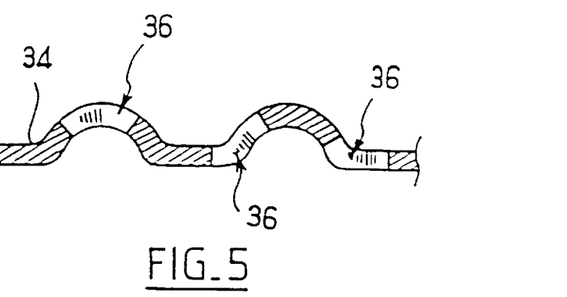
FIG. 5 is a view in section on V—V of the wall of FIG. 4.

With reference to FIGS. 3 to 5, the spool 20 comprises a cartridge 32 which has a cylindrical exterior face in surface-to-surface contact with the face of the duct 24, and two, front and rear, end walls 34. The walls 34 have a generally flat circular shape. However, in transverse profile, each wall 34 has undulations. In addition, it has orifices 36 of circular shape when viewed in plan, formed in locally non-planar portions of the wall. Thus, the orifices 36 have skewed, that is to say non-planar, contours. The cartridge 32 contains a product 35, here in the form of granules of plastic containing a volatile substance such as a fragrance in the adsorbed state. These may, for example, be polymer granules marketed by ELF ATOCHEM under the brand name PEBAX. The spool 20 and the cartridge 32 here constitute the reservoir.

The spool 20 is placed in the body 4, the shaft 28 extending into the duct 12 and out of the body 4. The spool 20 can move in terms of rotation with respect to the body 4 about the coincident axes 14 and 30. The spool 20 occupies the same place in the body whatever its rotational position about the axis 14. Action on the shaft 28 allows the spool 20 to be placed in any one of the following positions. In the open position, or diffusing position, the ducts 8 and 24 are coaxial and in the continuation one of the other. When air enters one of the openings 11, it passes in succession, and in this order, through a portion of the duct 8, a portion of the duct 24, an end wall 34 of the cartridge 32, the product 35, the other end wall 34 of the cartridge, the other portion of the duct 24, the other portion of the duct 8 and the second opening 11. On passing between the granules 35, the air becomes laden with desorbed fragrance which it diffuses through the second opening 11. The undulations in the walls 34 of the cartridge 32 allow this cartridge to be completely filled with granules without these blocking the orifices 36. The air can therefore pass right through the cartridge.

In the closed position, the spool 20 extends with the axis 26 of the duct 24 perpendicular to the axis 10 of the duct 8 of the body 4. The wall of the spool 20 extends facing the two portions of the duct 8 which it closes off. The cartridge 32 is isolated from the body 4 and from the openings 11, this isolation being sealed by virtue of the seals 19.

It is also possible to have a position of partial opening (or closure) when the axes 10 and 26 of the ducts 8 and 24 are slightly inclined one with respect to the other. In this position, only a small air communication is permitted from one of the openings 11 to the other through the cartridge 32.

To allow the spool 20 to be introduced into the body 2, the latter has, for example, a main part 2a which is widened out on its face that has the first opening 11 and has a threaded interior housing of axis 10. The body 2 further also comprises an attached part 2b defining the largest part of the face which has the first opening 11 and has a threaded cylindrical exterior face designed to be screwed into the housing in the main part 2a. Each of the two parts—the main part 2a and the attached part 2b—defines a hemisphere of the spherical interior face 16. The spool 20 is housed in the main part 2a before this part is attached to the attached part 2b.

Figure 6:
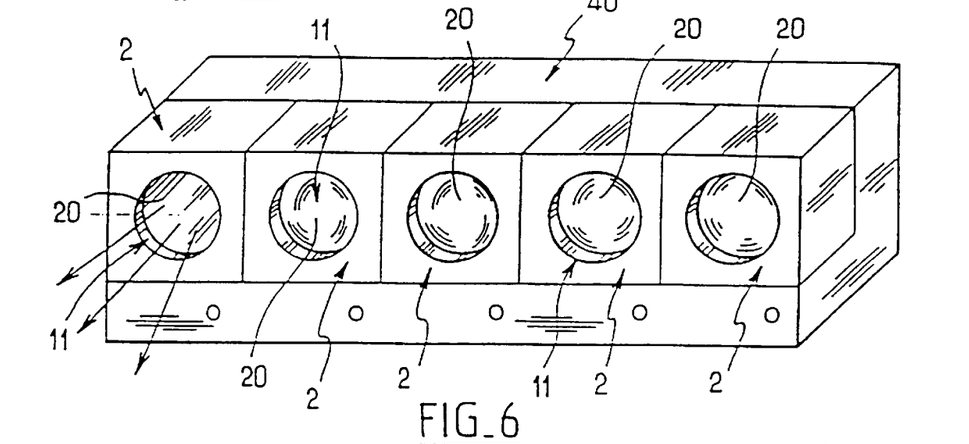
FIG. 6 is a perspective view of a diffusion device supporting diffusers according to FIG. 3.
Figure 7:
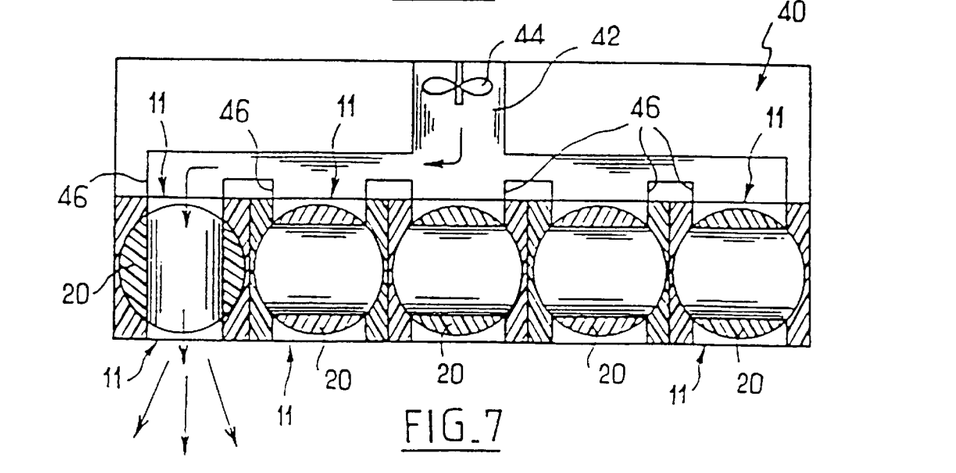
FIG. 7 is a view in cross section of the device of FIG. 6.

With reference to FIGS. 6 and 7, a diffusion device according to a preferred embodiment of the invention is a scent organ and comprises a support 40 which has a series of places designed to accept diffusers 2 placed side by side with the front openings 11 facing in the same direction, the series of places constituting a module. The support comprises means for holding the diffusers in their places by clipping-together. Each place has an actuator, not depicted, designed to collaborate with the axis 30 of the associated diffuser 2 to maneuver the spool 20 with respect to the body 4. The support 40 comprises a primary duct 42 containing a blower 44 and connected to a series of secondary pipes 46 opening into the respective places facing the rear opening 11 of the ducts 8 of the diffusers. The support 40 comprises means for switching the blower 44 on and for choosing the position—closed, partially open or open—of each of the diffusers 2. Each of the diffusers 2 comprises a cartridge 32 associated with a different substance, for example a fragrance. The diffusers are all supplied with air by the blower 44, the common source of air, which takes in its air at the rear part of the support 40.

When all the diffusers 2 are closed, to diffuse one or more of the fragrances, all that is required is for the associated diffuser or diffusers 2 to be brought into a partially or fully open position. The blower 44 supplies the open diffuser or diffusers with air. The diffusion of a volatile substance using the diffuser occurs without a rise in temperature, thus avoiding degrading the substance that is to be diffused. The closed diffusers are subjected, by the blower 44, to a slight raised pressure. However, each diffuser 2 that is in a closed position prevents the delivery of fragrance even in the event of a raised pressure.

When a diffuser 2 which was initially in an open position is placed in a closed position, diffusion of the associated fragrance ceases. In addition, the cartridge 32 is isolated from the outside of the device. There is therefore no phenomenon of persistent smell. In addition, the product 35 containing the fragrance is shut away and can thus be kept for a long time. The support 40 will advantageously comprise polarizing means for mounting each diffuser 2 in the correct position in its space. It would be possible to provide means known per se for preventing the diffuser 2 from being maneuvered for diffusing the fragrance unless it is in place on the support. The partially-open position allows the intensity of the fragrance diffused to be adjusted. A stepping motor will make it possible to choose the partially-open position of each diffuser with great precision.

A second preferred embodiment will now be described with reference to FIGS. 8 to 27, with numerical references increased by 100.

Figure 8:
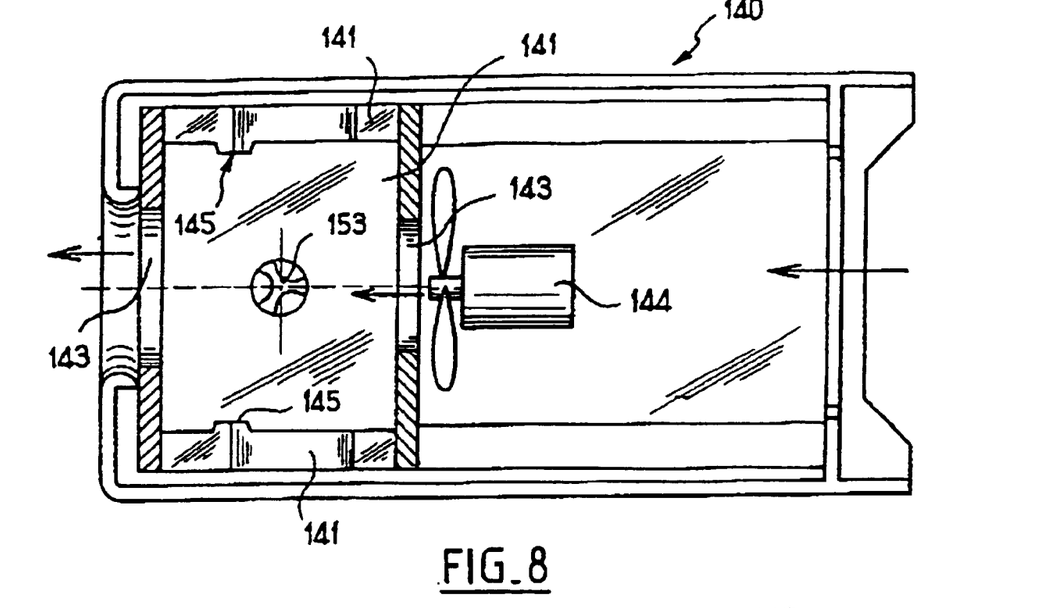
FIGS. 8 and 9 are respective views from above in section and from the right in section of a support for a diffusion device according to a second embodiment of the invention.
Figure 9:
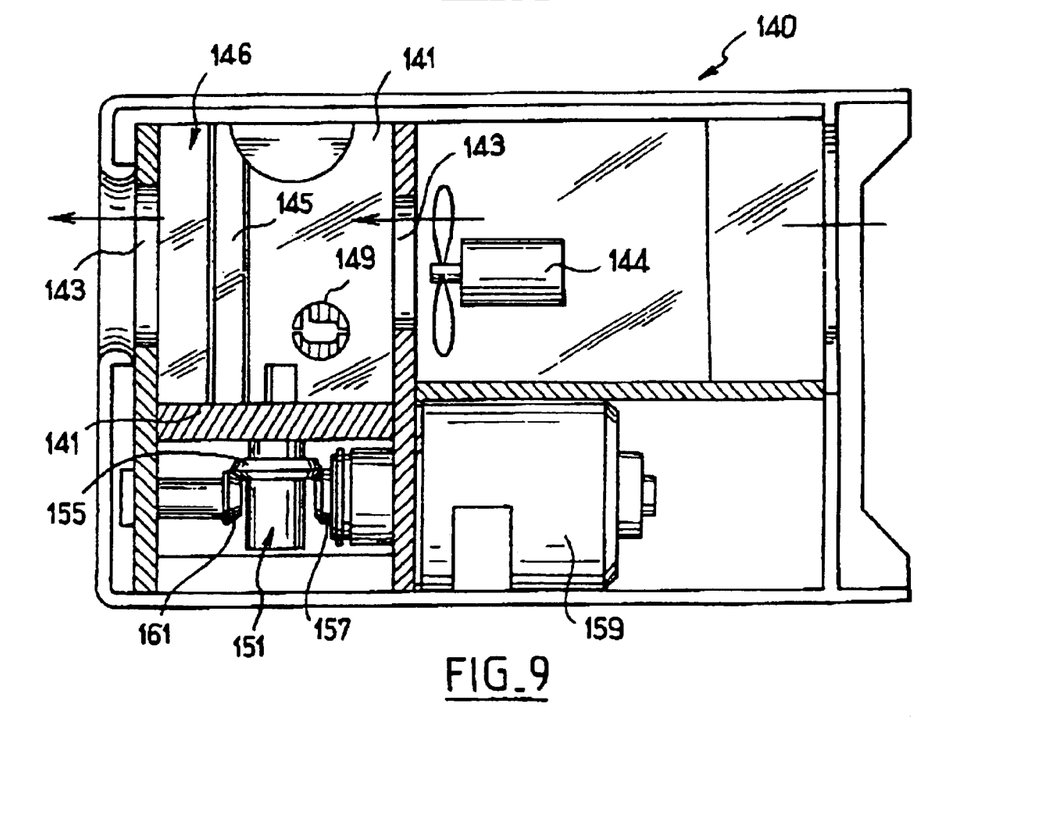

The support 140 illustrated in FIGS. 8 and 9 is able to accept a diffuser 102 illustrated in FIGS. 10 to 20. The diffuser 102 comprises a body 104 comprising a hollow casing 105. This has an exterior shape of cubic overall shape and an interior shape of cylindrical overall shape. The casing 105 has a cylindrical interior face 116 of axis 110 and a lower orifice 112 of axis 114, the axes 110 and 114 being secant and perpendicular to each other. The cylindrical face 116 is broken by a flat 121 extending in a plane perpendicular to the axis 114 and having the orifice screw locations for this purpose. The plates form openings 111.

With reference to FIGS. 17 to 20, the diffuser 102 comprises a spool 120 which, here too, has a convex spherical exterior face 122 and a cylindrical interior face 124 of axis 126 coaxial thereto. The cylindrical interior face 124 has, near its axial ends, two annular grooves 129. The grooves 129 respectively accept two gratings 134 identical to the gratings 34 in the first embodiment. The spool 120 is filled with granules in the chamber delimited between the two gratings 134 via the interior face 124. In this instance it is therefore practically the entire interior volume of the spool which is occupied by the granules. The spool has a flat lower exterior face 131 parallel to the axis 126 and, therein, a rectangular flat-bottomed cavity 133.

Figure 20:
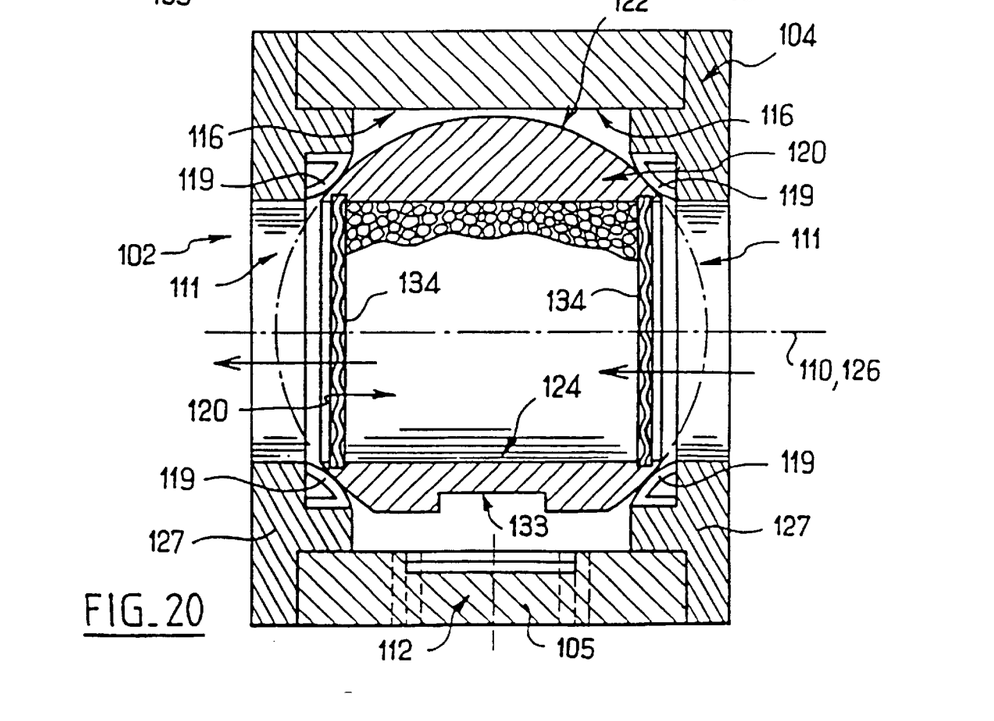
FIG. 20 is a view in axial section illustrating the spool of FIG. 19 between the two plates of FIG. 15.
Figure 21:
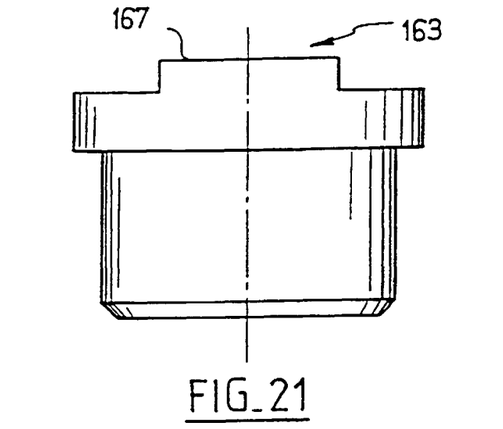
FIGS. 21 to 24 are views from the front, in axial section, from above and from beneath, of the drive shaft of the diffuser of FIG. 10.
Figure 22:
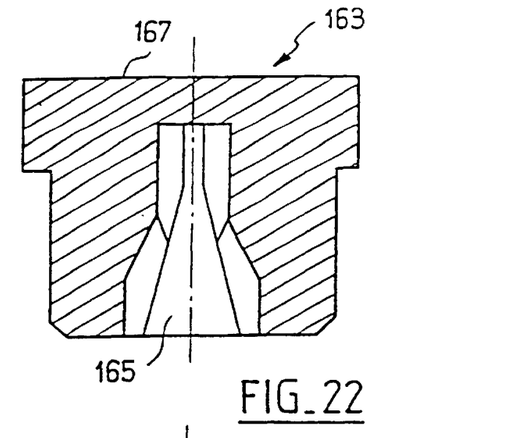
Figure 23:
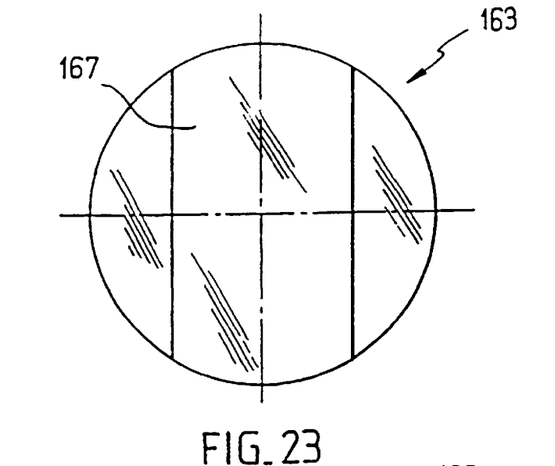
Figure 24:
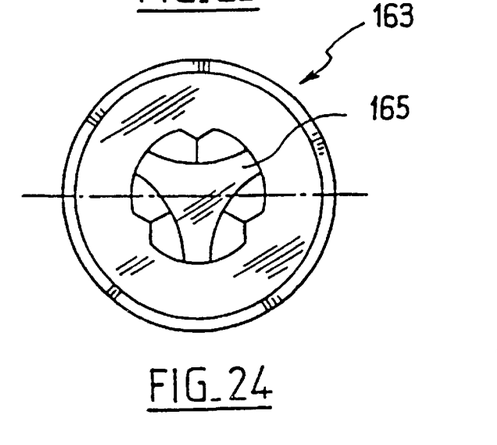
Figure 25:
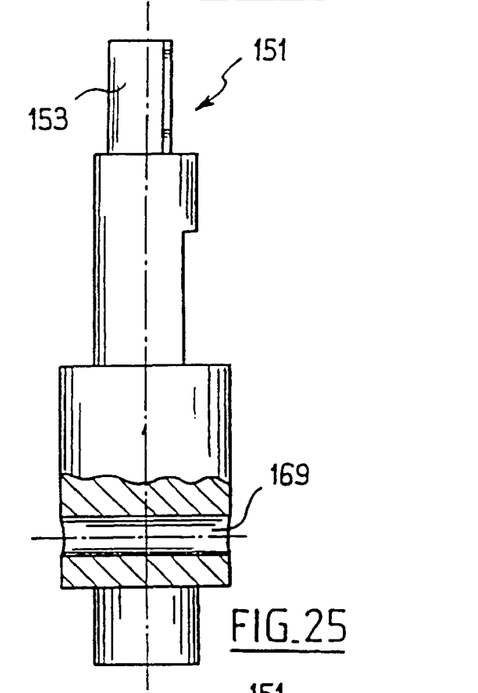
FIGS. 25 and 26 are elevations, partially in axial section, and from above, of the drive shaft of the support of FIG. 8.
Figure 26:
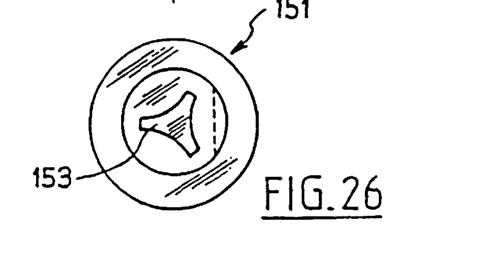
Figure 27:
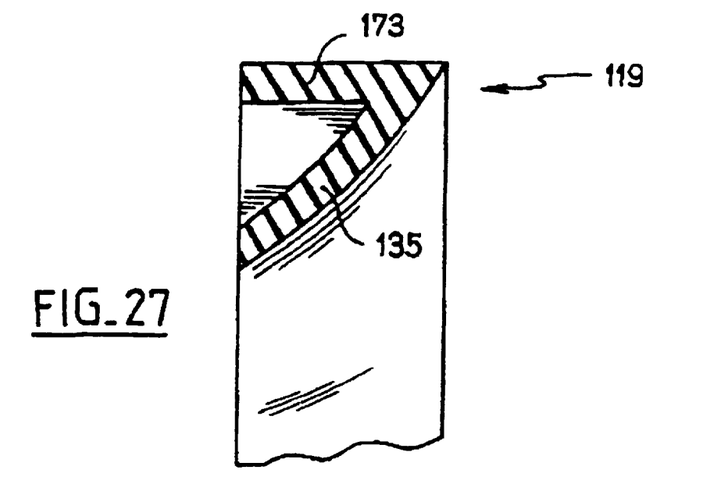
FIG. 27 is a view in axial section of a seal of the diffuser of FIG. 10.
Figure 28:
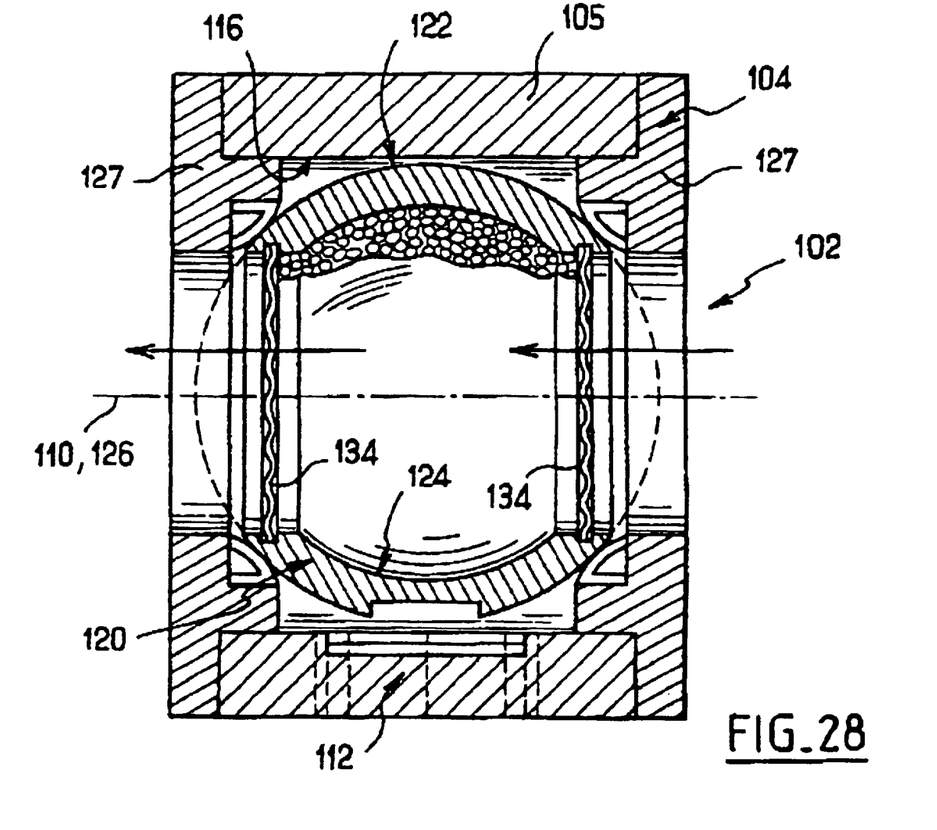
FIG. 28 is a view similar to FIG. 20, illustrating an alternative form.

As illustrated in FIG. 20, the spool 120 is housed coaxially in the body 104. The exterior spherical face 122 of the spool extends facing the plates 127 and the interior cylindrical face 116 of the casing. Each plate has an interior shoulder accepting a seal 119 of circular annular shape depicted in FIGS. 20 and 27. This seal has a "V" profile. It has a base 173 parallel to the axis 110 and a lip 135 connected to an innermost edge of the base and locally parallel to the spherical face 122 with which it comes into contact. In the open position illustrated in FIG. 20, the seals 119 extend very close to the gratings 134, around these. In the closed position, the gratings 134 extend facing the interior face 116, between the two seals which isolate these gratings from the outside.

With reference to FIGS. 8 and 9, the support 140 comprises walls 141 delimiting a housing that accepts the diffuser 102, approximately of the same shape thereas, having two openings 143 intended to face the openings 111 of the diffuser. The housing has an upper opening 146 for introducing the diffuser by sliding downward. The support comprises a blower 144 capable of sending air into the upstream opening 143. As a preference, to reduce noise, this blower will be replaced by a turbine.

The vertical side walls 141 forming the housing have, in their portion closest to the downstream opening 143, a vertical rib 145. The vertical side walls of the diffuser 102 likewise have a slot 147 capable of accepting the corresponding rib 145. Ribs and slots constitute polarizing means for introducing the diffuser 102 into the housing in a predetermined correct position.

Figure 10:
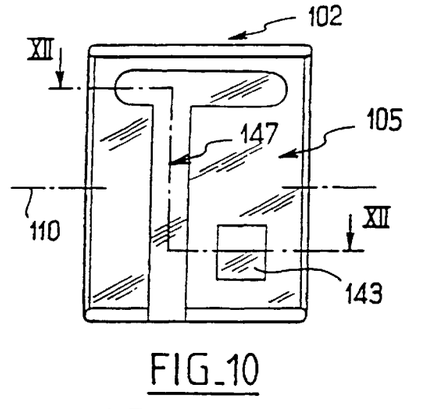
FIGS. 10 and 11 are respective views from the right and from the front of the housing of a diffuser intended to be accepted in the support of FIGS. 8 and 9.
Figure 11:
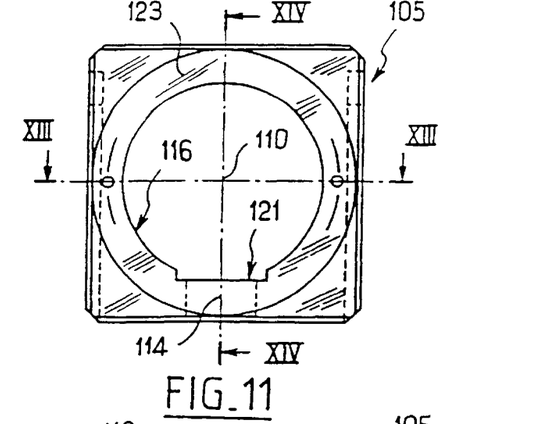
Figure 12:
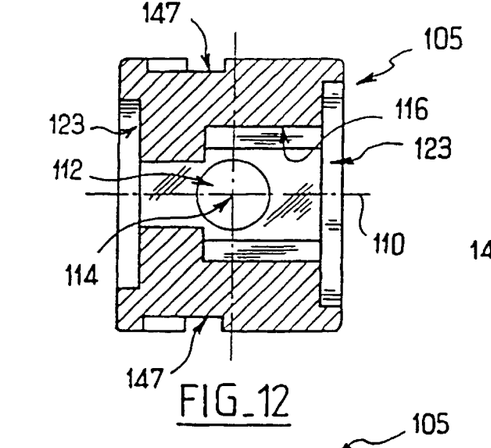
FIGS. 12, 13 and 14 are views of the housing of the diffuser in section on XII—XII, XIII—XIII and XIV—XIV of FIGS. 10 and 11.
Figure 13:
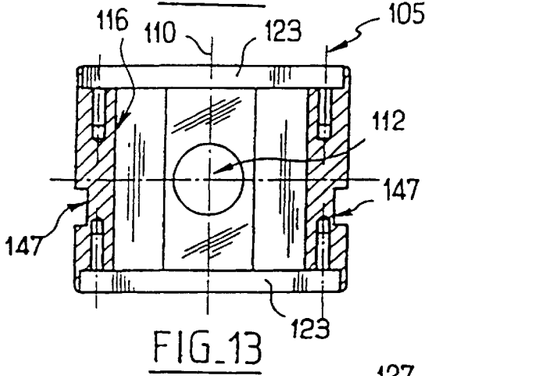
Figure 14:
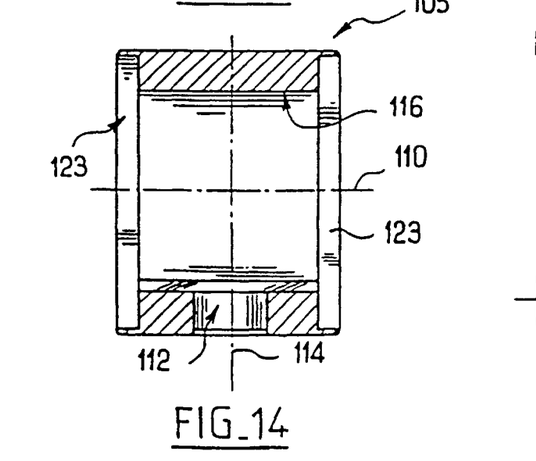
Figure 15:
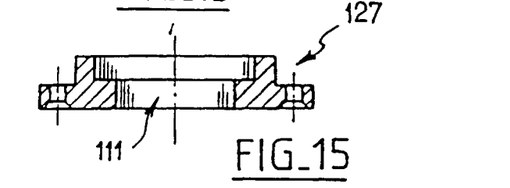
FIGS. 15 and 16 are respective views in axial section and from the front of a blanking plate for the housing of FIGS. 10 to 14.
Figure 16:
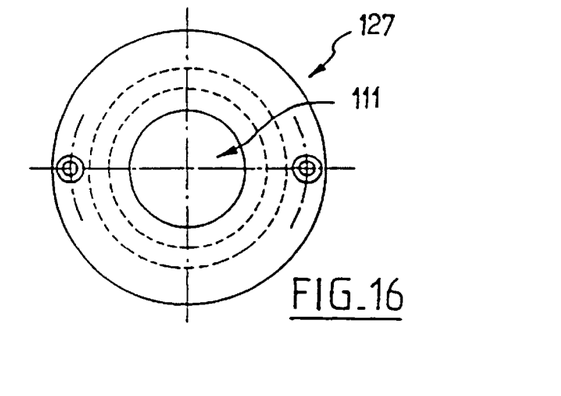
Figure 17:
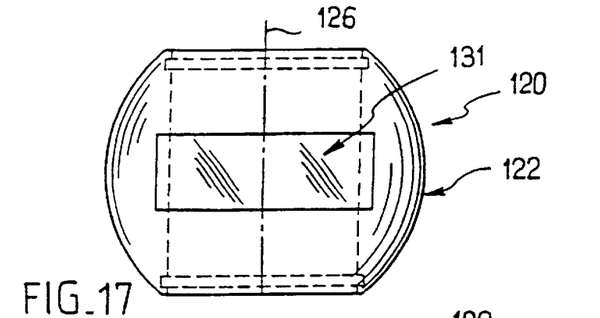
FIGS. 17, 18 and 19 are views from beneath, from the front and in axial section of a spool to be housed in the housing of FIGS. 10 to 14.
Figure 18:
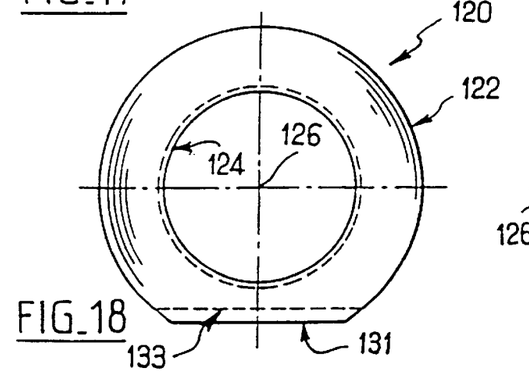
Figure 19:
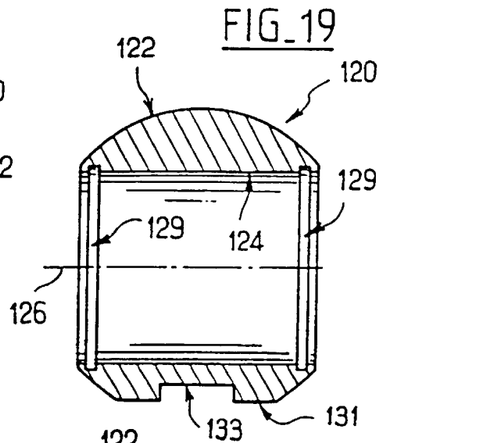

Moreover, the diffuser 102 may comprise electronic identification means such as a chip associated with reading means 143 accessible on a side face of the diffuser and illustrated in FIG. 10. The support 140 will then comprise a microprocessor and means 149 for dialog with the reading means 143 of the diffuser housed in the housing. These various electronic elements will constitute means for electronically identifying the diffuser 102 accepted by the support 140, for polarizing purposes when, according to the circumstances in which the support 140 is used, it is desirable for only certain predetermined diffusers 102 to be accepted in the support. This will be the case, for example, when the support is used for promotional purposes to promote one or more fragrances and must therefore accept only the diffuser or diffusers corresponding to this or these fragrances.

In the support 140, the lower wall 141 forming the housing has, passing through it, a drive shaft The support 140, particularly when it is available to the public, may be designed to be operated by a single push-button. Provision may be made for action on this push-button to trigger the switching-on of the blower 144 and, at the same time, the opening of the diffuser. A time delay closes the diffuser and switches off the blower at the end of an adjustable predetermined period of time. This version is well suited to the testing of a fragrance at a sales outlet.

Figure 29:
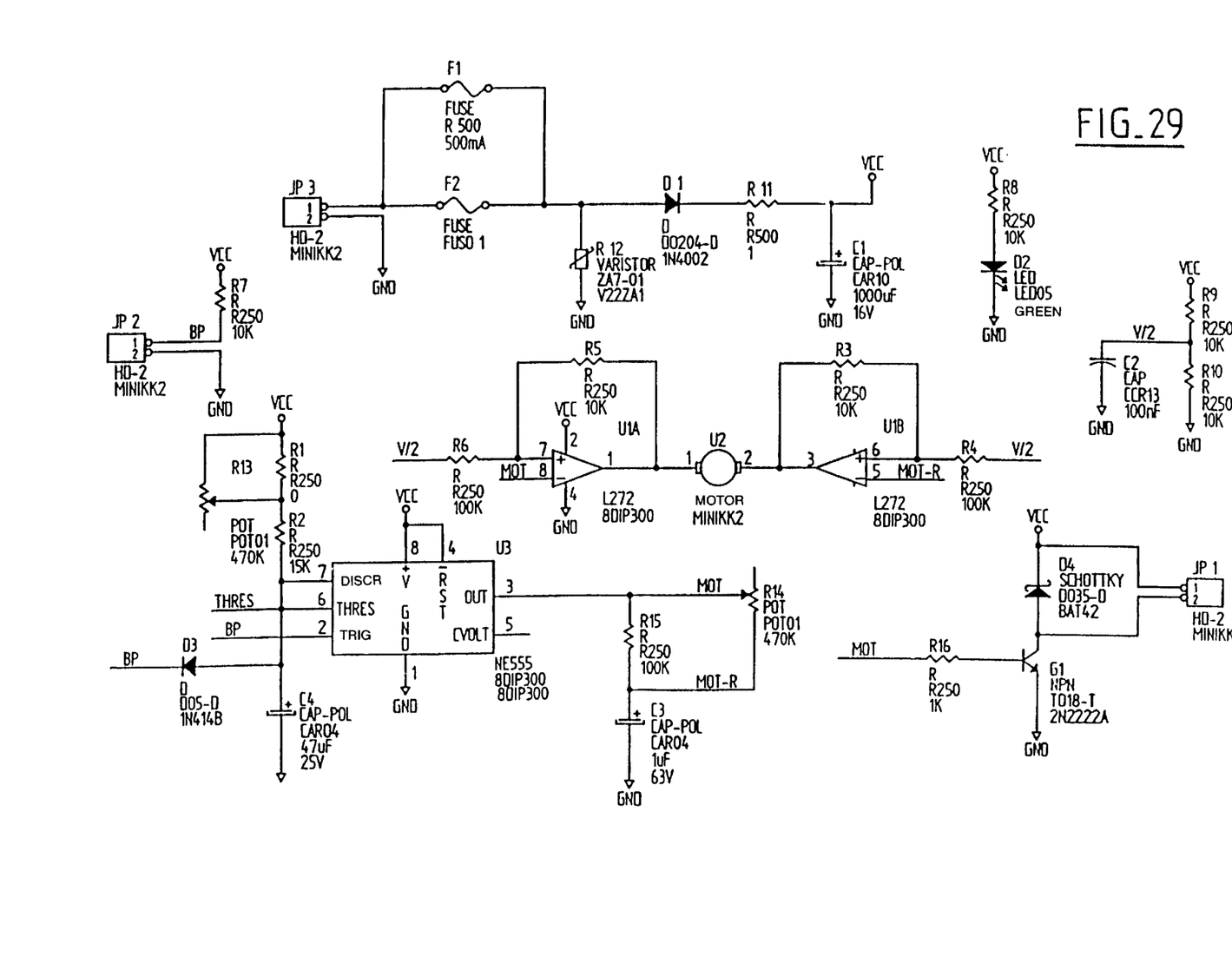
FIG. 29 is a circuit diagram for an electronic control circuit of the support.

An electronic control circuit for the support 140 allowing operation such as this is illustrated in FIG. 29. When the user presses the push-button, the blower starts up and the valve opens. When the intended period of time (about ten seconds) has elapsed, the blower stops and the valve closes again. If the user presses the button again, the cycle recommences. Likewise, if the user keeps the button depressed, the duration of the cycle is lengthened.

The timer function is provided by an NE555 (U3) which is mounted as a retriggerable monostable. The duration of time delay T is adjustable according to the following formula:

$$T=0.693\times(R13+R12)\times C4 \text{ with } C4=47 \mu F; R2=16 k;$$

R13 variable from 0 to 470 k.

The duration can therefore vary from 0.5 seconds to 15.8 seconds. In a series-production version, the potentiometer could be replaced by a resistor R1, the resistance of which would be adjusted for the desired time. The duration is lengthened if the potentiometer is turned in the clockwise direction.

The blower 144 is controlled via a transistor amplifier by the output of the NE555. The diode D4 acts as a free wheel to limit the overvoltage associated with inductive phenomena.

The motor 159 is controlled by a double power amplifier L222 (U1). The time for which power is applied to the motor is fixed by the RC network (R14, C4). This time can vary from 0 to 5 seconds.

The components D1, R11, C1, R12, F1 and F2 are used to protect the circuit.

D1 protects against reversal of polarity.

R11 and C1 form an RC network to regulate current spikes to improve EMC compatibility.

R12 clips overvoltages.

F1 or F2 are fuses to protect against short circuits. F1 is a filament-type fuse which places the card definitively out of action in the event of a fault. F2 is a resettable fuse which places the card out of action only when the fault is present. Maintenance of cards with the F2 fuse will therefore be less intensive.

The card may be powered by a mains wall power outlet with a power of at least 6 VA, unregulated, supplying 12 V at 500 mA. As a preference, the voltage of 12 V under load is to be guaranteed in order to maintain correct speed for the motor 159 used for closing and opening the valve or spool. If the power supply is too weak, the valve will not open fully.

A green LED visually indicates that the electronics are under power.

An eight-pin mini KK connector provides connections for the motor, the blower, the push-button and the power jack.

In a multimedia application, the diffuser according to the invention may be controlled by the UBS port of a computer.

The polarizing functions could alternatively be provided by reliefs for the coupling of the drive shafts 151 and 163 so that only certain diffusers 102 can be associated with certain supports 140.

One of the gratings 134 could be molded integrally with the spool 120.

In the diffuser, the chip could be used to store various data such as the date of manufacture, product code, etc.

The outlet of the support could be provided with a removable position-adjustable nozzle so as to give the best sense of smell according to the user's position.

When the diffuser 2, 102 has a single spherical face, this may be provided on the body 4, 104, the spool 20, 120 having a cylindrical exterior face.

The spherical face or faces may be replaced by a face with a profile that is curved in a plane radial to the axis of rotation and the curvature of which is always in the same direction, that is to say has no point of inflection.

Furthermore, in another embodiment, the diffuser 2 could be used directly, without a support 40. The fragrance would then be diffused without forced-air circulation. The diffuser could, for example, be worn around the user's neck. The sealed nature of the diffuser would even allow the user to bathe with it.

The substances to be diffused may be fragrances, for example to appeal to the sense of smell in certain places, or to present fragrances in a store. These may be pheromones for repelling or attracting insects or animals. The wearing of the diffuser about the user's person therefore affords good protection against dangerous insects. It may be a deodorizing, sanitizing or bactericide substance.

The orifices 36 may have a non-circular shape, for example an elliptical or polygonal shape, the walls 34, 134 being flat.

The characteristics relating to the orifices in the wall retaining the granules may be employed independently of the shape of the faces of the diffuser.

As a replacement for the blower 44, 144, the device 40, 140 could comprise a source of compressed inert gas.

The diffusion device 40, 140 could comprise a number of modules each comprising a number of diffusers 2, 102, thus defining a rectangular matrix of diffusers 2, 102.

The diffuser may have various configurations which differ greatly from those just described.

The diffuser and the diffusion device according to the invention allow smells of fragrances to be diffused without the use of a solvent, particularly alcohol, which is forbidden by certain national legislation for the diffusion of smells under certain circumstances, particularly in public.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed is:

1. A diffuser of a volatile substance comprising a body which has at least one opening and a reservoir for a product containing a volatile substance, said reservoir being mounted to move in said body between a diffusing position which allows a gas to flow through said product and into said at least one opening, and a closed position in which said product is isolated from said opening, said reservoir and said body having respective faces extending in facing relation to each other, one of said faces is spherical and includes at least one element which makes a seal between said body and said reservoir in the closed position.

2. The diffuser according to claim 1, wherein said spherical face is the reservoir.

3. The diffuser according to claim 1, wherein said reservoir rotably moves with respect to said body.

4. The diffuser according to claim 3, wherein said faces each have symmetry of revolution about an axis of rotation.

5. The diffuser according to claim 1, wherein said faces are spherical.

6. The diffuser according to claim 1, wherein said reservoir has a spherical interior face.

7. The diffuser according to claim 1, wherein with said at least one opening being a first opening, said body has a second opening designed so that, in the diffusing position, gas flows into said second opening, then through said product then into said first opening.

8. The diffuser according to claim 1, wherein said reservoir comprises a removable cartridge containing said product.

9. The diffuser according to claim 1, wherein said product comprises granules containing said volatile substance in an adsorbed state.

10. The diffuser according to claim 1, wherein said reservoir has a wall exhibiting orifices, each said orifice having a contour shape forming a passage for gas when a spherical granule is resting against said at least one orifice.

11. The diffuser according to claim 10, wherein said orifices have a skewed circular contour.

12. The diffuser according to claim 10, wherein said wall is undulating.

13. A device for diffusing a volatile substance having at least one diffuser, said at least one diffuser comprising a body which has at least one opening and a reservoir for a product containing a volatile substance, said reservoir being mounted to move in said body between a diffusing position which allows a gas to flow through said product and into said at least one opening and a closed position in which said product is isolated from said opening, said reservoir and said body having respective faces extending in facing relation to each other, one of said faces being spherical and including at least one element which makes a seal between said body and said reservoir in the closed position, and a support designed to accept said at least one diffuser simultaneously.

14. The device according to claim 13, wherein said support comprises means for controlling said position of said reservoir of said at least one diffuser.

15. The device according to claim 13, wherein said support comprises means for circulating a gas through said at least one diffuser in a diffusing position.

16. The device according to claim 15, including an organ pipe, and said support includes said at least one diffuser, and said gas-circulating means being common to said at least one diffuser.

17. The device according to claim 13, and further comprising polarizing means for accepting said diffuser in said support in at least one predetermined position.

18. The device according to claim 13, and further comprising polarizing means for accepting at least one predetermined diffuser in said support.

* * * * *